United States Patent [19]

Kawaguchi et al.

[11] Patent Number: 5,656,506

[45] Date of Patent: Aug. 12, 1997

[54] DRY DETECTION REAGENT CONTAINING ACRYLAMIDE/STYRENE COPOLYMER PARTICLES IMMOBILIZING AN IMMUNOLOGICALLY ACTIVE SUBSTANCE

[75] Inventors: Haruma Kawaguchi, Yokohama; Takeshi Miyazaki, Ebina, both of Japan

[73] Assignee: Canon Kabushiki Kaisha, Tokyo, Japan

[21] Appl. No.: 456,622

[22] Filed: Jun. 1, 1995

Related U.S. Application Data

[63] Continuation of Ser. No. 174,468, Dec. 28, 1993, abandoned, which is a continuation of Ser. No. 729,164, Jul. 12, 1991, abandoned.

[30] Foreign Application Priority Data

Jul. 13, 1990 [JP] Japan .................................. 2-184071
Jul. 13, 1990 [JP] Japan .................................. 2-184072

[51] Int. Cl.$^6$ .................... G01N 33/546; G01N 33/545; C12N 11/08
[52] U.S. Cl. .................... 436/534; 435/7.92; 435/180; 436/531; 530/815
[58] Field of Search .................... 435/7.1, 180, 7.92; 436/531, 533, 534; 530/815

[56] References Cited

U.S. PATENT DOCUMENTS

| | | | |
|---|---|---|---|
| 4,181,636 | 1/1980 | Fischer | 260/8 |
| 4,563,431 | 1/1986 | Pauly et al. | 436/533 |

FOREIGN PATENT DOCUMENTS

| | | |
|---|---|---|
| 0195623 | 9/1986 | European Pat. Off. . |
| 0360088 | 3/1990 | European Pat. Off. . |
| 0462644 | 12/1991 | European Pat. Off. . |
| 2345723 | 10/1977 | France . |
| 322733 | 6/1975 | Germany . |
| 52-117420 | 10/1977 | Japan . |
| 53-52620 | 5/1978 | Japan . |
| 53-12966 | 5/1978 | Japan . |
| 58-73866 | 5/1983 | Japan . |
| 2027031 | 2/1980 | United Kingdom . |

OTHER PUBLICATIONS

Hoshino, et al., Kobunshi Ronbunshu, 1985, 42(5), 305–310.

*Primary Examiner*—David M. Naff
*Attorney, Agent, or Firm*—Fitzpatrick, Cella, Harper & Scinto

[57] ABSTRACT

A dry detection reagent for detecting an immunologically active substance is prepared containing solid fine polymer particles immobilizing a substance immunologically active for the substance detected. The polymer particles are prepared by one of the following methods: a) ternary copolymerization of a monomer having carboxyl groups, a monomer having amino groups and styrene or its derivatives; b) binary copolymerization of a monomer having carboxyl groups and styrene or its derivatives, and reacting part of the carboxyl groups with a bifunctional amine such as ethylene diamine to provide amino groups; or c) copolymerizing styrene or its derivatives with a monomer having amide groups, and converting part of the amide groups to amino groups and carboxyl groups with the Hofmann reaction, or hydrolyzing part of the amide groups to form carboxyl groups. Preferably, styrene and acrylamide having amide groups are copolymerized and part of the amide groups are hydrolyzed to carboxyl groups or part of the amide groups are converted to carboxyl groups and amino groups by the Hofmann reaction. The immunologically active substance used for detecting is immobilized on the particles and the particles are dried to produce the dry reagent. To carry out detection, the dry reagent is dispersed in a liquid, the liquid is mixed with a sample containing the substance to be detected which becomes bound to the substance immobilized on the particles and the bound substance is optically detected. The dry reagent is stable during storage and has excellent re-dispersibility in a liquid.

6 Claims, 1 Drawing Sheet

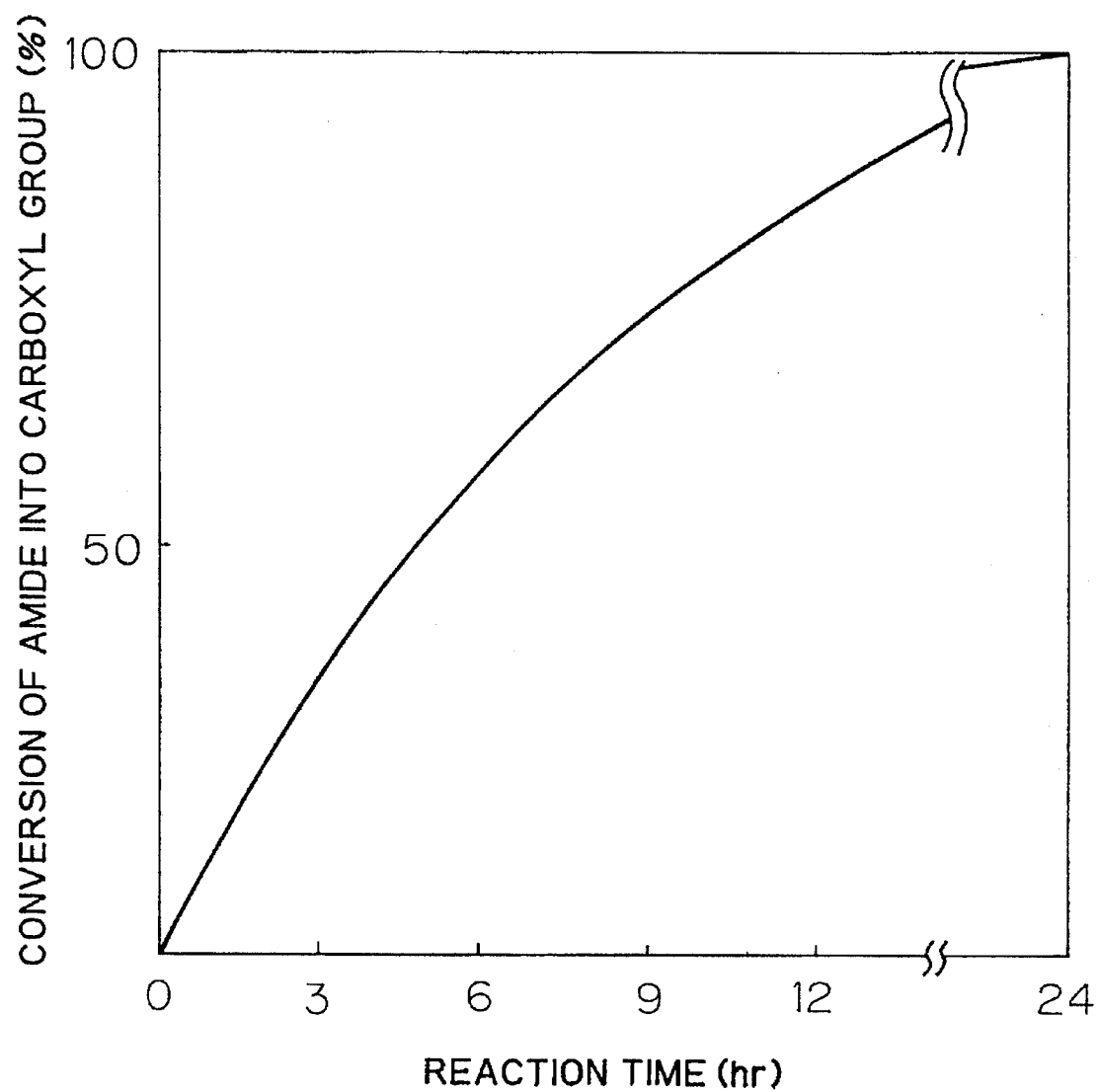

DRY DETECTION REAGENT CONTAINING ACRYLAMIDE/STYRENE COPOLYMER PARTICLES IMMOBILIZING AN IMMUNOLOGICALLY ACTIVE SUBSTANCE

This application is a continuation of application Ser. No. 08/174,468 filed Dec. 28, 1993, now abandoned, which is a continuation of application Ser. No. 07/729,164 filed Jul. 2, 1991, now abandoned.

BACKGROUND OF THE INVENTION

1. Field of the invention

This invention relates to a detection reagent which comprises solid fine particles immobilizing an immunologically active substance for a substance to be detected in a test sample and can be used for various immunological detections and assays.

2. Related Background Art

The latex agglutination immunoassay method (LAIA), which assays presence of antigens, etc. by allowing a substance which reacts specifically with the immunologically active substance as mentioned below such as antigen, etc. to react with a dispersion containing solid fine particles such as polystyrene, etc. having an immunologically active substance such as antibody, etc. carried thereon dispersed in a liquid medium such as water, etc. (latex reagent) and observing the agglutination which occurs thereby has been found by J. M. Singer et al, Am. J. Med., 21, 888 (1956), and thereafter various investigations have been made.

The assaying method utilizes LAIA which determines the extent of agglutination by sight. Although quantitative assay may be difficult, the method has the advantage that the assay is simple and the result can be obtained in a short time, therefore it has been practically applied and widely utilized for various detections.

Further, in recent years, it has become possible to make a quantitative assay by LAIA by evaluating the extent of agglutination corresponding to the reaction by way of optical change according to the optical method utilizing an optical instrument, and such quantitative assay is now widely practiced.

The latex reagent to be used for LAIA has solid fine particles having an antibody, immobilized thereon dispersed in a liquid medium as described above.

However, since a dispersion of solid fine particles is an essentially unstable system and, when stored for a long time, agglutination of solid fine particles is liable to occur and, when agglutination has occurred, there will ensue such a problem as lowering in assay sensitivity, etc. Also, when thawed after storage in frozen state, no dispersed state of solid fine particles can be reproduced thereby making it impossible to be utilized for reagent in most cases.

Accordingly, the latex reagent has required special concern regarding storage.

As a method for solving such a problem in storage stability, the method of enhancing storage stability as dry product by drying the latex reagent as the dispersion has been investigated.

For example, Japanese Patent Application Laid-open No. 58-73866 discloses a method in which an agglutinatable immunoreagent such as latex reagent, etc. is placed in a capillary and freeze dried before storage.

However, the latex reagent brought to a dry state has been sufficiently applicable for a qualitative assay, but has proved to be insufficient for application to a quantitative assay by use of an optical method.

More specifically, when the latex reagent is dried according to such method as evaporation, spray drying, freeze drying, vacuum drying, etc., agglutination between solid fine particles will occur, whereby uniform dispersed state of solid fine particles during re-suspension can no longer be obtained and no quantitative analysis with good reproducibility can be done.

As a method for improving the re-dispersibility of the dry latex reagent, for example, Japanese Patent Application Laid-Open No. 52-117420 discloses a method in which a latex reagent added with water-soluble sugars such as lactose, etc. therein is freeze dried under such state to give a dry product.

According to this method, although re-dispersibility of the dry latex reagent is considerably improved by addition of water-soluble sugars, there still remains a problem that no sufficient re-dispersibility demanded in quantitative analysis by use of an optical method can be obtained.

Accordingly, there is the method of increasing the amount added of the additive such as sugars for enhancing re-dispersibility, but use of a large amount of additive exerts deleterious influence such as sensitivity lowering on the immunological reaction, and the increase of the amount added is limited.

Further, there is also the method of obtaining a more uniform re-dispersed state by stirring the dispersion for a long time or at high stirring intensity. However, stirring treatment under strong conditions may result in destruction of the bound state between the immunologically active substance and the solid fine particles or destruction of the immunologically active substance itself. Therefore depending on the bound state between the immunologically active substance and the solid fine particles or the kind of the immunologically active substances, these methods cannot be applied.

SUMMARY OF THE INVENTION

Accordingly, an object of the present invention to provide a detection reagent for LAIA which can be also suitably applied for quantitative analysis by use of an optical method.

It is also another object of the present invention is to provide a detection reagent for LAIA which can be stably stored under dry state.

Still another object of the present invention is to provide a detection reagent for LAIA which is excellent in re-dispersibility into a liquid medium from dry state, and can be also suitably applied to quantitative analysis by use of an optical method.

That is, the present invention provides a detection reagent comprising solid fine particles immobilizing an immunologically active substance for substance to be detected in a test sample, wherein said solid fine particles comprise a modified polystyrene having amino group and carboxyl groups.

Also, the present invention provides a detection reagent comprising solid fine particles immobilizing an immunologically active substance for substance to be detected in a test sample, wherein said solid fine particles comprise a modified polystyrene having amide groups and carboxyl groups.

BRIEF DESCRIPTION OF THE DRAWINGS

The Figure is a graph showing a relationship between the treatment time and conversion of amide group to carboxyl group in the treatment of a styrene/acrylamide copolymer in an alkali aqueous solution.

DETAILED DESCRIPTION OF THE PREFERRED EMBODIMENTS

First, the solid fine particles comprising a modified polystyrene in the detection reagent of the present invention, which is the first invention, refers to a polymer comprising a site having an amino group and a carboxyl group and a site having styrene or a polymer of the site having styrene substituted with amino groups and carboxyl groups or a polymer comprising styrene substituted with amino groups and carboxyl groups and a site having an amino group and a carboxyl group. The solid fine particles can be prepared according to various known methods and, for example, the following methods can be utilized.

a) The method in which a monomer having a carboxyl group, a monomer having an amino group and at least one selected from styrene and styrene derivatives are subjected to ternary polymerization to obtain a fine particles of modified polystyrene.

b) A monomer having a carboxyl group and at least one monomer selected from styrene and styrene derivatives are subjected to binary polymerization, and a part of the carboxyl groups on the surface of copolymer fine particles are converted to amino groups with a bifunctional amine, as for example ethylene diamine.

c) The component A comprising at least one selected from styrene and styrene derivatives and the component B comprising a monomer having an amide group are polymerized, and the surface of the copolymer fine particles obtained is modified by the Hofmann reaction to introduce amino groups and carboxyl groups.

Among these methods, the method c) is more suitable in that more stable fine particles with uniform particle sizes can be obtained. In the method c), amide groups are converted to amino groups simultaneously with formation of carboxyl groups through hydrolysis of amide groups as the side reaction, and there is also the advantage that the ratio of amino groups and carboxyl groups can be varied by suitable setting the conditions.

The ratio of amino group and carboxyl group in the modified polystyrene constituting the solid fine particles ranges from 0.01 to 100, more suitably from 0.5 to 20, of carboxyl group per one amino group.

In the following, the case according to the method c) is described.

Examples of the styrene derivatives to be used for the component A may include α-methylstyrene, 2,4-dimethylstyrene, α-ethylstyrene, p-vinylstyrene, p-isopropylstyrene, m-phenylstyrene, α-chlorostyrene, p-chlorostyrene, p-methoxystyrene, m-aminostyrene, p-cyanostyrene and the like.

As the component B, for example, (meth)acrylamide and its derivatives such as N-methyl(meth)acrylamide, N-phenyl(meth)acrylamide, N,N-(diethylaminoethyl)(meth)acrylamide, N,N-dimethyl(meth)acrylamide or the like, methylenebis(meth)acrylamide, etc. can be used individually or as a combination of two or more kinds of these.

For copolymerization of the component A and the component B, various known methods can be utilized.

For example, various polymerization methods can be utilized, including emulsion polymerization by use of a water-soluble radical initiator in an aqueous liquid medium in the presence of anionic surfactant, nonionic surfactant, etc.; soap-free emulsion polymerization by use of a water-soluble radical initiator in an aqueous liquid medium without use of surfactant; suspension polymerization in the presence of a protective colloid such as partially saponified polyvinyl alcohol, polyvinyl pyrrolidone, etc.; precipitation polymerization in which polymerization is carried out in a liquid medium which dissolves a vinyl monomer but does not dissolve a polymer; etc.

The molar ratio of the component A and the component B in the copolymer can be made within the range of, for example, from 1:0.5 to 1:0.001.

The reaction conditions in polymerization may be suitably set depending on the particle size, etc. of the copolymer solid fine particles to be obtained.

The particle size of the solid fine particles is not particularly limited, but in view of dispersibility of the detection reagent in liquid medium, particularly re-dispersibility of dry reagent, for example, it may be preferably within the range from 0.05 µm to 5 µm, particularly within the range from 0.1 µm to 2 µm. More specifically, when the particle size is less than 0.05 µm, it becomes difficult to re-disperse dry reagent, while if it exceeds 5 µm, precipitation of solid fine particles, etc. in dispersion is liable to occur, whereby no stability of the reagent as dispersion can be obtained.

The solid fine particles obtained are then treated by the Hofmann reaction to derive amino groups and carboxyl groups onto the surface thereof. The Hofmann reaction as shown by the following formula is a method in which a primary carboxylic amide is reacted with bromine (or chlorine) in an alkali aqueous solution to obtain a primary amine with carbon atoms less by one, partially forming carboxyl group in the side reaction.

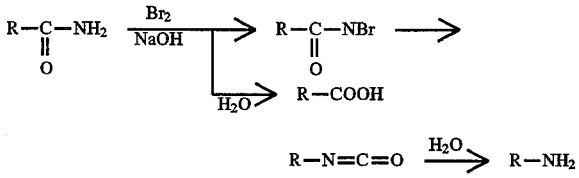

The solid fine particles comprising a modified polystyrene in the detection reagent of the present invention, which is the second invention, refers to a polymer comprising a site having an amide group and a carboxyl group and a site having styrene or a polymer of the site having styrene substituted with amide groups and carboxyl groups or a polymer comprising a site having styrene substituted with amide groups and carboxyl groups and a site having an amide groups and a carboxyl group. For example, it can be obtained by ternary polymerization of a monomer having an amide group, a monomer having carboxyl group and at least one monomer selected from styrene and styrene derivatives. Also, it can be obtained by binary polymerization of a styrene derivative having an amide group and a styrene derivative having a carboxyl group.

It can also be it can be obtained by the method in which the component A comprising at least one selected from styrene and styrene derivatives and the component B comprising a monomer having an amide group can be copolymerized, and a part of the amide groups possessed by the copolymer fine particles obtained are hydrolyzed to be converted to carboxyl groups.

Among these methods, the method of the latter utilizing hydrolysis of an amide group is suitable in that fine particles with uniform sizes are obtained.

According to this method, carboxyl groups are formed by hydrolysis of amide groups, and there is also the advantage that the ratio of amide groups and carboxyl groups can be varied by suitably setting the conditions.

The ratio of amide groups and carboxyl groups in the modified polystyrene constituting the solid fine particles is within the range of 0.01 to 1000, more preferably from 0.5 to 100, of carboxyl group per one amide group.

In the following, the method of utilizing hydrolysis of amide group is described.

As the styrene derivatives to be used for the component A, those as mentioned above can be included.

Also as the component B, those as mentioned above can be used.

For polymerization of the component A and the component B, various known methods can be utilized. The polymerization methods are also as described above.

The molar ratio of the component A and the component B in the copolymer can be chosen, for example, within the range from 1:0.5 to 1:0.001.

The reaction conditions in polymerization can be suitably set depending on the particle size of the copolymer solid fine particles to be obtained.

The particle size of the solid fine particles in the second invention is not particularly limited, but, in view of the dispersibility of the detection reagent in liquid medium, particularly re-dispersibility of dry reagent, etc., similarly as the particle size in the first invention, is preferably within the range from 0.05 μm to 5 μm, particularly within the range from 0.1 μm to 2 μm.

In the second invention, the solid fine particles obtained are subsequently subjected to hydrolysis to convert a part of amide groups to carboxyl groups.

Such hydrolysis can be carried out, for example, in an alkaline aqueous solution such as aqueous sodium hydroxide solution, aqueous potassium hydroxide solution, etc.

The reaction conditions in hydrolysis such as alkali concentration, reaction time, reaction temperature, etc. may be suitably chosen depending on the desired conversion of amide groups to carboxyl groups and stability of the solid fine particles themselves, etc.

For example, under the conditions employed in the Reference Example as described below, the conversion of amide groups to carboxyl groups can be varied by varying the hydrolysis time, and by setting the hydrolysis time on the basis of the results, a desired conversion of amide groups to carboxyl groups can be obtained.

As the immunologically active substance to be immobilized on the surface of the solid fine particles in the first and second inventions, various substances necessary for immunoassay of the substance to be detected can be employed.

For example, there can be employed immunoglobulins such as IgG, IgM, IgE, etc.; plasma proteins such as complement, CRP, ferritin, $\alpha_1$-microglobulin, $\beta_2$-microglobulin, etc. and antibodies to these; tumor markers such as $\alpha$-fetogrotein, carcinoembryonic antigen (CEA), prostatic acid phosphatase (PAP), CA-19-9, CA-125 and antibodies to these; hormones such as luteinizing hormone (LH), follicle stimulative hormone (FSH), human chorionic gonadotropin (hCG), estrogen, insulin, etc. and antibodies to these; viral infection related substances such as HBV related antigens (HBs, HBe, HBc), HIV, ALT, etc. and antibodies to these; bacteria such as Corynebacterium diphtheriae, Clostridium botulinum, Mycoplasma, treponema pallidum, etc. and antibodies to these; protozoa such as Toxoplasma, Trichomonas, Lieshmania, Tripanozoma, Malaria and antibodies to these; drugs including antieplectics such as phenitoin, phenobarbital, etc., cardiovascular drugs such as quinidine, digoxinine, etc., antiasthmatics such as theophylline, etc., antibodies such as chloramphenicol, gentamycine, etc. and antibodies to these; enzymes, extracellular toxins (streridin O, etc.) and antibodies to these; and so on.

As the immobilization method of immunologically active substances onto solid fine particles, for example, various chemical and/or physical binding methods used for immobilization of enzymes, etc. disclosed in Immobilized Enzyme (Kodansha, 1975, edited by Ichiro Chihata), etc. can be utilized.

For example, there can be utilized the method in which an immunologically active substance is bound to solid fine particles by covalent bonding by use of a polyaldehyde such as glutaraldehyde, etc., the method in which an immunologically active substance is bound to solid fine particles by use of carbodiimide or Woodward reagent K as the condensing agent as disclosed in Japanese Patent Publication No. 53-12966, Japanese Patent Application Laid-open No. 53-52620.

Also, to the solid fine particles or the immunologically active substance, a dye for making easier detection of agglutination during immunoassay or a labelling agent such as fluorescent dye may be also bound.

Immobilization of an immunologically active substance onto solid fine particles should be preferably practiced in an aqueous liquid medium. As such aqueous liquid medium, water, a mixture of water with an organic solvent, etc. can be utilized. As the organic solvent, alcohols or ketones compatible with water can be utilized.

The immobilization reaction may be also carried out in a buffer solution such as phosphate buffer physiological saline (PBS), Tris-hydrochloride buffer solution, etc. optionally in the presence of an inert protein such as bovine serum albumin, surfactant, etc. for the purpose of stabilizing the solid fine particles or prevention of nonspecific agglomeration in the reaction system.

The pH value of the reaction mixture in the immobilization reaction can be made generally from 6 to 10, preferably from 7 to 9.

The concentration of the solid fine particles in the reaction mixture can be made generally from 0.01 to 5.0% by weight.

The solid fine particles having an immunologically active substance immobilized thereon can be dispersed in a liquid medium for immunoassay to obtain a reagent for assay as a dispersion.

As the aqueous liquid medium to be used for preparation of the dispersion of the reagent of the present invention, water of mixed solvents of water and organic solvents compatible with water such as alcohols, ketones, etc. may be employed. In the dispersing medium, buffers, proteins, surfactants, water-soluble polymeric compounds, etc. may be suitably added.

The buffer is added to adjust pH to the optimum value, because the antigen-antibody reaction is generally susceptible to the influence from pH of the solvent and, for example, a phosphate or Tris HCl buffering agent may be employed. Proteins are added for the purpose of preventing non-specific reactions and, for example, bovine serum albumin, gelatin, etc. may be employed. Also, for the purpose of controlling the detection sensitivity, a surfactant or a water-soluble polymeric compound such as polyethylene glycol, etc. may be added.

Further, by preparing an appropriate dispersion of solid fine particles having an immunologically active substance immobilized thereon, removing the liquid medium from the dispersion and drying the particles, a dry reagent can be obtained.

As the drying method, such method as evaporation, spray drying, freeze drying, vacuum drying, etc. can be utilized, and it is desirable to perform drying at a temperature of 60° C. or lower, preferably 30° C. or lower. Among these methods, freeze drying is preferable in that the sensitivity of the reagent can be constantly maintained.

The dry reagent can be re-dispersed in a liquid medium for immunoassay to be used for assay as a dispersion reagent.

In the following, the present invention is described in more detail by referring to Examples.

EXAMPLE 1

1-1. Synthesis of solid fine particles:

Into a polymerization vessel of 300 ml volume equipped with a reflux condenser, a stirrer and a thermometer were added 160 ml of water, 0.50 g of sodium tetraborate ($Na_2B_4O_7.10H_2O$) and 2.0 g of acrylamide, and the mixture was heated to 70° C.

After the air in the vessel was replaced with $N_2$ by introducing $N_2$ gas into the polymerization vessel for 30 minutes, 1.7 g of potassium persulfate was added as the polymerization initiator, and polymerization reaction was carried out at 70° C. for one hour under stirring by a stirrer at 300 rpm.

Next, 40 g of styrene was added into the polymerization vessel, the mixture was stirred under the same conditions for 4 hours, and further stirring was continued with addition of 2 g of acrylamide under the same conditions for 5 hours to obtain fine particles of a styrene/acrylamide copolymer.

The dispersion was cooled to room temperature, and a part of the styrene/acrylamide copolymer fine particles synthesized were recovered and dried. Spherical particles with uniform particle sizes of 0.76 μm were observed by means of a transmission electron microscope.

The styrene/acrylamide copolymer fine particles were recovered by centrifugation from the above dispersion, further washed three times with distilled water, and then a dispersion which contains copolymer fine particles with a solid content of 20% by weight.

To 5 ml of this dispersion were added 5 ml of 10% aqueous sodium hypochlorite solution and 10ml of 10% aqueous sodium hydroxide solution, and the reaction was carried out at 4° C. for 6 hours, thereby effecting the treatment of the solid fine particles surface (according to the Hofmann reaction) to obtain modified polystyrene fine particles.

After the reaction, the reaction mixture was neutralized with hydrochloric acid, the solid fine particles comprising the modified polystyrene obtained were washed four times with distilled water, followed by repetitive centrifugation and decantation, and then a dispersion of solid fine particles with a solid content of 10% by weight.

Electroconductivity titration of the dispersion of the modified polystyrene particles was carried out, and from the electroconductivity titration curve obtained, the surface densities of amino groups and carboxyl groups of the modified polystyrene fine particles were determined.

The surface density of amino groups was found to be 2.0 unit/nm$^2$ and that of carboxyl groups 0.9 unit/nm$^2$.

1-2. Immobilization of antibody:

To 0.5 ml of the dispersion of the solid fine particles of the modified polystyrene obtained in the operation of the above item 1-1 were added 5 ml of N/15 phosphate buffer solution (pH 8.0) and 0.12 g of 1-ethyl-3-(3-dimethylaminopropyl)-carbodiimide hydrochloride (WSC) and the mixture was shaken at room temperature for 3 hours.

Next, the solid fine particles were washed three times with N/15 phosphate buffer solution (pH 8.0) to recover the solid particles.

To the solid fine particles recovered was added 5 ml of a CRP antibody solution (prepared by diluting the IgG fraction of the anti-human CRP sheep serum produced by Cooper Biomedical Inc. with PBS to be made 1 mg/ml of IgG with), and the mixture was shaken at room temperature for three hours to obtain antibody-sensitized solid fine particles.

The antibody-sensitized solid fine particles obtained from the reaction mixture were recovered by centrifugation, washed with N/15 phosphate buffer solution (pH 8.0) and dispersed in PBS (pH 7.2), which contains bovine serum albumin in 1% concentration to obtain a dispersion of the antibody-sensitized solid fine particles.

1-3. Preparation of dry reagent:

The dispersion of the antibody-sensitized solid fine particles obtained in the operation 1-2 as described above was freeze dried under a reduced pressure in liquid nitrogen to obtain a dry reagent.

1-4. Evaluation of re-dispersibility was as follows:

2.0 mg of the dry reagent obtained in the operation 1-3 as described above was placed into a glass cell, 1 ml of PBS was added thereto, and sonication stirring was carried out at an output of 25 W (20 kHz) for 30 seconds to re-disperse the antibody-sensitized solid fine particles into PBS, thereby preparing a reagent for assay as the dispersion.

The re-dispersibility of the antibody-sensitized solid fine particles in the reagent for assay obtained was measured by a flow cytometer and dispersibility (M %) was calculated.

The dispersibility (M %) was calculated from the following equation.

$$\text{dispersibility } (M \%) = \frac{\text{Number of non-agglutinated particle}}{\text{Number of total particle}}$$

The results are shown in Table 1.

1-5. Quantification of antigen:

Predetermined concentration series of the standard CRP serum (produced by Igaku Seibutsugaku Kenkyusho) were prepared, and each concentration sample (0.5 ml) and the reagent for assay (0.5 ml) obtained by re-dispersing the dry reagent according to the operation as described above were individually reacted at 37° C., and the agglomerated state by the antigen-antibody reaction was measured with spectral absorbance at 633 nm. As the result, at the CRP concentration of 6 μg/ml or more, CRP was quantified.

EXAMPLE 2

To 5 ml of a dispersion (solid content 20% by weight) of the styrene/acrylamide copolymer fine particles obtained in the item 1-1 in Example 1 were added 10% aqueous sodium hypochlorite solution (5 ml) and 10% aqueous sodium hydroxide solution (10 ml), and the reaction was carried out at 10° C. for 6 hours, thereby affecting the treatment of the solid fine particles surface by the Hofmann reaction to obtain modified polystyrene fine particles.

After the reaction, the reaction mixture was neutralized with hydrochloric acid, washed 4 times according to centrifugation with distilled water to obtain a dispersion of the modified polystyrene fine particles with a solid content of 10% by weight. The surface densities of amino groups and carboxyl groups of the modified polystyrene fine particles in the dispersion obtained were measured in the same manner as in the item 1-1 in Example 1, and as the result, the surface density of amino groups was found to be 3.2 unit/nm$^2$ and that of carboxyl groups 0.2 unit/nm$^2$.

By use of the dispersion of the modified polystyrene fine particles, immobilization of the antibody (CRP), preparation of dry reagent, re-dispersion into PBS and quantification of CRP were conducted in the same manner as in the items 1-2 to 1-5 in Example 1.

The result of the dispersibility (M %) calculated in the same manner as in the item 1-4 in Example 1 during re-dispersion is shown in Table 1.

In the reagent for assay (dispersion) of the present Example, CRP was quantified at concentrations of 6 μg/ml or more.

EXAMPLE 3

To 0.5 ml of the modified polystyrene fine particles obtained in Example 2 were added 5 ml of N/15 phosphate buffer solution (pH 8.0) and 0.5 ml of a CRP antibody solution (10 mg/ml), and the mixture was shaken at room temperature for 3 hours to obtain antibody-sensitized solid fine particles.

The antibody-sensitized solid fine particles obtained were recovered by centrifugation, further washed with N/15 phosphate buffer solution (pH 8.0), followed by dispersion into PBS (pH 7.2) to obtain a dispersion of the antibody-sensitized solid fine particles.

By use of the dispersion, preparation of dry reagent, re-dispersion into PBS and quantification of CRP were conducted in the same manner as in the items 1-3 to 1-5 in Example 1.

The result of the dispersibility (M %) calculated in the same manner as in the item 1-4 in Example 1 during re-dispersion is shown in Table 1.

In the reagent for assay (dispersion) of the present Example, CRP was quantified at concentrations of 6 ug/ml or more.

EXAMPLE 4

From sn anti-human α-fetoprotein (horse) (AFP) serum (produced by Midori Juji Co.), the IgG fraction was fractionated according to the column chromatography by use of Sepharose (produced by Pharmacia Co.) having protein A immobilized thereon, which was diluted with a 0.1M phosphate buffer solution (pH 7.2) to a concentration of 10 mg/ml to prepare an IgG fraction antibody solution.

To 0.5 ml of a dispersion of the modified polystyrene fine particles obtained in the item 1-1 in Example 1 was added 5 ml of a 0.05M sodium borate buffer solution (pH 8.0) containing 10% glutaraldehyde, and the mixture was shaken at 0° C. for 10 minutes.

After completion of shaking, washing according to centrifugation with N/15 phosphate buffer solution (pH 8.0) was carried out three times to recover the solid particles. To the recovered solid particles were added 1 ml of the antibody solution previously prepared and 4 ml of N/15 phosphate buffer solution (pH 8.0), and the mixture was shaken at room temperature for 3 hours to obtain the antibody-sensitized solid fine particles.

The antibody-sensitized solid fine particles were recovered by centrifugation, washed with N/15 phosphate buffer solution (pH 8.0) and then dispersed in PBS to obtain a dispersion.

By use of the dispersion, preparation of dry reagent, re-dispersion into PBS were conducted in the same manner as in the items 1-3 to 1-4 in Example 1.

The result of dispersibility (M %) calculated in the same manner as in the item 1-4 in Example 1 during re-dispersion is shown in Table 1.

Further, by use of the standard AFP serum (produced by Kyowa Yukakagaku Co.) in place of the standard CRP serum, AFP was quantified in the same manner as in the item 1-5 in Example 1.

In the reagent for assay (dispersion) of the present Example, AFP was quantified at concentrations of 2 μg/ml or more.

Comparative example 1

To 0.5 ml of a dispersion in distilled water (solid content 10%) of a polystyrene latex (produced by Nippon Synthetic Rubber Co.) with a particle size of 0.721 μm were added 5 ml of N/15 phosphate buffer solution (pH 8.0) and a CRP antibody solution (10 mg/ml), and the mixture was shaken at room temperature for 3 hours to obtain the antibody-sensitized solid fine particles.

The antibody-sensitized solid fine particles obtained were recovered by centrifugation, further washed with N/15 phosphate buffer solution (pH 8.0) and then dispersed into PBS (pH 7.2) containing bovine serum albumin at 1% concentration to obtain a dispersion of the antibody-sensitized solid fine particles.

By use of the dispersion, preparation of dry reagent, redispersion into PBS and quantification of CRP were conducted in the same manner as in the items 1-3 to 1-5 in Example 1.

The result of the dispersibility (M %) calculated in the same manner as in the item 1-4 in Example 1 during re-dispersion is shown in Table 1.

In the reagent for assay (dispersion) of the Comparative Example, CRP was quantified at a concentration of 15 μg/ml.

TABLE 1

| | | Carrier | Antibody | Surface density of amino group (unit/ $nm^2$) | Surface density of carboxyl group (unit/ $nm^2$) | Average particle side (μm) | Dispersibility (%) |
|---|---|---|---|---|---|---|---|
| Example | 1 | Modified poly-styrene | CRP | 2.0 | 0.9 | 0.76 | 98.4 |
| | 2 | | " | 3.2 | 0.2 | 0.76 | 97.9 |
| | 3 | | " | 3.2 | 0.2 | 0.76 | 97.4 |
| | 4 | | AFP | 2.0 | 0.9 | 0.76 | 98.1 |
| Comparative example | | Polystyrene | CRP | 0 | 0 | 0.721 | 82.6 |

REFERENCE EXAMPLE 1

[Synthesis of solid fine particles]

Into a polymerization vessel of 300 ml volume equipped with a reflux condenser, a stirrer and a thermometer were added 160 ml of water, 0.50 g of sodium tetraborate ($Na_2B_4O_7 \cdot 10H_2O$) and 2.0 g of acrylamide, and the mixture was heated to 70° C.

After the air in the vessel was replaced with $N_2$ by introducing $N_2$ gas into the polymerization vessel for 30 minutes, 1.7 g of potassium persulfate was added as the polymerization initiator, and polymerization reaction was carried out at 70° C. for one hour under stirring by a stirrer at 300 rpm.

Next, 40 g of styrene was added into the polymerization vessel, the mixture was stirred under the same conditions for 4 hours, and further stirring was continued with addition of 2 g of acrylamide under the same conditions for 5 hours to obtain a dispersion of fine particles of a styrene/acrylamide copolymer which were not agglutinated.

The dispersion was cooled to room temperature, and a part thereof was taken out to dry the styrene/acrylamide copolymer fine particles synthesized. Spherical particles with uniform particle sizes of 0.76 μm were observed by means of a transmission electron microscope.

The styrene/acrylamide copolymer fine particles were recovered by centrifugation from the above dispersion, further washed three times with distilled water, and obtained a dispersion which contained copolymer fine particles with a solid content of 20% by weight.

To 25 ml of the dispersion was added 100 ml of 20% aqueous sodium hydroxide solution to carry out the treatment at 30° C., and hydrolysis for converting amide groups to carboxyl groups was carried out.

At appropriate periods of the reaction time from 0 to 24 hours, the reaction mixture was sampled, and the amounts of the carboxyl groups formed were calculated from the electroconductivity titration curve to determine the conversion of amide groups to carboxyl groups.

The results are shown in FIG. 1.

From the results in FIG. 1, about 99% of amide groups were converted to carboxyl groups with the reaction time of hydrolysis time of 24 hours. Therefore, by setting suitably the reaction time of hydrolysis, the ratio of amide groups and carboxyl groups can be controlled.

EXAMPLE 5

1-1. Preparation of modified polystyrene fine particles:

To 25 ml of a dispersion in distilled water (solid content 20% by weight) of the styrene/acrylamide copolymer fine particles obtained in Reference Example 1 was added 100 ml of 20% aqueous sodium hydroxide solution, and hydrolysis treatment was carried out at 30° C. for 24 hours to obtain modified polystyrene fine particles.

After completion of the reaction, the reaction mixture was neutralized with hydrochloric acid, the solid fine particles comprising the modified polystyrene recovered by centrifugation, washed 4 times with distilled water to prepare a dispersion with a solid content of 10%.

The conversion of amide groups to carboxyl groups in the solid fine particles in the dispersion obtained was calculated from the electroconductivity titration curve to be 99%. The surface density of carboxyl groups was found to be 5.0 unit/nm$^2$.

1-2. Immobilization of antibody:

To 0.5 ml of the dispersion of the solid fine particles of the modified polystyrene obtained in the operation 1-1 above were added 5 ml of N/15 phosphate buffer solution (pH 8.0) and 0.12 g of 1-ethyl-3-(3-dimethylaminopropyl)-carbodiimide hydrochloride (WSC) and the mixture was shaken at room temperature for 3 hours.

Next, the solid fine particles were washed three times with N/15 phosphate buffer solution (pH 8.0) to recover the solid particles.

To the recovered solid fine particles was added 5 ml of a CRP antibody solution (prepared by diluting the IgG fraction of the anti-human CRP sheep serum produced by Cooper Biomedical Inc. with PBS to be made 1 mg/ml of IgG), and the mixture was shaken at room temperature for three hours to obtain antibody-sensitized solid fine particles.

The antibody-sensitized solid fine particles were recovered by centrifugation, washed with N/15 phosphate buffer solution (pH 8.0) and dispersed in PBS (pH 7.2) containing bovine serum albumin at 1% concentration to obtain a dispersion of the antibody-sensitized solid fine particles.

1-3. Preparation of dry reagent:

The dispersion of the antibody-sensitized solid fine particles obtained in the operation 1-2 as described above was freeze dried under a reduced pressure in liquid nitrogen to obtain a dry reagent.

1-4. Evaluation of re-dispersibility was as follows:

2.0 mg of the dry reagent obtained in the operation 1-3 as described above was placed into a glass cell, 1 ml of PBS was added thereto, and sonication stirring was carried out at an output of 25 W (20 kHz) for 30 seconds to re-disperse the antibody-sensitized solid fine particles into PBS, thereby preparing a reagent for assay (dispersion).

The re-dispersibility of the antibody-sensitized solid fine particles in the reagent for assay obtained was measured by a flow cytometer and dispersibility (M %) was calculated.

The results are shown in Table 2.

1-5. Quantification of antigen:

Predetermined concentration series of the standard CRP serum (produced by Igaku Seibutsugaku Kenkyusho) were prepared, and each concentration sample (0.5 ml) and the reagent for assay (0.5 ml) obtained by re-dispersing the dry reagent according to the operation as described above were individually reacted at 37° C., and the agglomerated state by the antigen-antibody reaction was measured with spectral absorbance at 633 nm. The CRP concentration of 8 μg/ml or more, CRP was quantitated.

EXAMPLE 6

To 25 ml of a dispersion in distilled water (solid content 20% by weight) of the styerene/acrylamide copolymer fine particles obtained in Reference example 1 was added 100 ml of 20% aqueous sodium hydroxide solution, and hydrolysis treatment was carried out at 30° C. for 7 hours to obtain a modified polystyrene.

After completion of the reaction, the reaction mixture was neutralized with hydrochloric acid, the solid fine particles comprising the modified polystyrene recovered by centrifugation, washed 4 times with distilled water to prepare a dispersion with a solid content of 10%.

The conversion of amide groups to carboxyl groups in the solid fine particles in the dispersion obtained was calculated from the electroconductivity titration curve to be 67%. The surface density of carboxyl groups was found to be 3.4 unit/nm$^2$.

By use of the dispersion of the modified polystyrene fine particles obtained, in the same manner as in the items 1-2 to 1-5 in Example 5, immobilization of the antibody (CRP), preparation of dry reagent, re-dispersion into PBS and quantification of CRP were conducted.

The result of dispersibility (M %) calculated in the same manner as in the item 1-4 in Example 5 is shown in Table 2.

In the reagent for assay (dispersion) of the present Example, CRP was quantified at a concentration of 8 μg/ml.

EXAMPLE 7

To 25 ml of a dispersion in distilled water (solid content 20% by weight) of the styerene/acrylamide copolymer fine particles obtained in Reference Example 1 was added 100 ml of 20% aqueous sodium hydroxide solution, and hydrolysis treatment was carried out at 30° C. for 10 minutes to obtain modified polystyrene fine particles.

After completion of the reaction, the reaction mixture was neutralized with hydrochloric acid, the solid fine particles comprising the modified polystyrene recovered by centrifugation, washed 4 times with distilled water to prepare a dispersion with a solid content of 10%.

The conversion of amide groups to carboxyl groups in the solid fine particles in the dispersion obtained was calculated from the electroconductivity titration curve to be 2%. The surface density of carboxyl groups was found to be 0.1 unit/nm$^2$.

By use of the dispersion of the modified polystyrene fine particles obtained, in the same manner as in the items 1-2 to 1-5 in Example 5, immobilization of the antibody (CRP), preparation of dry reagent, re-dispersion into PBS and quantification of CRP concentration were conducted.

The result of dispersibility (M %) calculated in the same manner as in the item 1-4 in Example 5 is shown in Table 2.

In the reagent for assay (dispersion) of the present Example, CRP was quantified at a concentration of 8 μg/ml.

EXAMPLE 8

From an anti-human α-fetoprotein (horse) (AFP) serum (produced by Midori Juji Co.), the IgG fraction was fractionated according to the column chromatography by use of Sepharose (produced by Pharmacia) having protein A immobilized thereon, which was diluted with a 0.1M phosphate buffer solution (pH 7.2) to a concentration of 10 mg/ml to prepare an IgG fraction antibody solution.

To 0.5 ml of a dispersion of the modified polystyrene fine particles obtained in the item 1-1 in Example 5 were added 5 ml of N/15 phosphate buffer solution (pH 8.0) and 0.12 g of WSC, and the mixture was shaken at room temperature for 3 hours.

After completion of shaking, 1 ml of the antibody solution previously prepared and 4 ml of N/15 phosphate buffer solution (pH 8.0) were added into the reaction mixture, and the mixture was shaken at room temperature for 3 hours to obtain the antibody-sensitized solid fine particles.

The antibody-sensitized solid fine particles were recovered by centrifugation, washed with N/15 phosphate buffer solution (pH 8.0) and then dispersed in PBS to obtain a dispersion.

By use of the dispersion, preparation of dry reagent, re-dispersion into PBS were conducted in the same manner as in the items 1-3 to 1-4 in Example 5.

The result of dispersibility (M %) calculated in the same manner as in the item 1-4 in Example 5 during re-dispersion is shown in Table 2.

Further, by use of the standard AFP serum (produced by Kyowa Yukakagaku Co.) in place of the standard CRP serum, AFP was quantified in the same manner as in the item 1-5 in Example 5.

In the reagent for assay (dispersion) of the present Example, AFP was quantified at concentrations of 1 ug/ml or more.

EXAMPLE 9

To 0.5 ml of the dispersion of the modified polystyrene fine particles obtained in Example 6 were added 5 ml of N/15 phosphate buffer solution (pH 8.0) and 0.5 ml of a CRP antibody solution (10 mg/ml), and the mixture was shaken at room temperature for 3 hours to obtain antibody-sensitized solid fine particles.

The antibody-sensitized solid fine particles obtained were recovered by centrifugation, further washed with N/15 phosphate buffer solution (pH 8.0) and then dispersed into PBS containing bovine serum albumin at 1% concentration to obtain a dispersion of the antibody-sensitized solid fine particles.

By use of the dispersion, in the same manner as in the items 1-3 to 1-5 in Example 5, preparation of dry reagent, re-dispersion into PBS and quantification of the antigen concentration were conducted.

The result of dispersibility (M %) calculated in the same manner as in the item 1-4 in Example 5 during re-dispersion is shown in Table 2.

In the reagent for assay (dispersion) of the present Example, CRP was quantified at a concentration of 9 μg/ml.

TABLE 2

| | | Carrier | Ratio of carboxyl group to amide group (carboxyl group: amide group) | Dispersibility (%) |
|---|---|---|---|---|
| Example | 5 | Modified poly-styrene | 99:1 | 97.8 |
| | 6 | | 67:33 | 98.2 |
| | 7 | | 2:98 | 98.0 |
| | 8 | | 99:1 | 97.1 |
| | 9 | | 67:33 | 97.6 |

The modified polystyrene fine particles having amino groups and carboxyl groups as the carrier used for the detection reagent of the present invention are excellent in dispersibility into the liquid medium composed mainly of water, and by forming them into a dispersion and using it as the detection reagent for LAIA, not only qualitative analysis but also quantitative analysis by use of the optical method can be performed.

Also, the detection reagent of the present invention is not only excellent in storage stability as the dry product, but also excellent in re-dispersibility, and the dispersion prepared by re-dispersion can be suitably used as one which gives results with good reproducibility to the qualitative analysis and the quantitative analysis by use of the optical method.

In preparing the dispersion by re-dispersion of the dry product, no stirring under special strong stirring condition is required, but a reagent for assay (dispersion) can be prepared within a short time without bringing about lowering in detection sensitivity, whereby shortening of the measurement time can be effected.

What is claimed is:

1. A process for detecting a first substance being immunologically active in a sample by using a diagnostic reagent, comprising the steps of;
   (a) preparing a dry diagnostic reagent including a second substance immunologically active with the first substance by the steps of;
      (i) providing solid fine particles consisting essentially of a copolymer consisting of styrene and acrylamide having amide groups as copolymerized monomers;
      (ii) incorporating carboxyl groups into the particles by hydrolyzing a part of the amide groups contained by the acrylamide of the copolymer, to obtain particles having carboxyl groups and amide groups in a ratio of 0.01 to 1,000 carboxyl groups per one amide group;
      (iii) combining the second substance with the particles having the carboxyl groups and the amide groups whereby the second substance becomes bound to the particles; and
      (iv) drying the particles containing the bound second substance to prepare the dry diagnostic reagent;

(b) dispersing the dry diagnostic reagent in a liquid;

(c) mixing the liquid in which the diagnostic reagent is dispersed with a sample containing the first substance to bind the first substance to the second substance; and (d) optically detecting the first substance bound to the second substance contained by the diagnostic reagent.

2. The process according to claim 1, wherein the ratio of the carboxyl groups to the amide groups is 0.5 to 100 carboxyl groups per one amide group.

3. A process for detecting a first substance which is immunologically active in a sample, comprising the steps of;

(a) preparing a dry diagnostic reagent including a second substance immunologically active with the first substance by the steps of;

(i) providing solid fine particles consisting essentially of a copolymer consisting of styrene and acrylamide having amide groups as copolymerized monomers;

(ii) incorporating carboxyl carboxyl groups into the particles by hydrolyzing a part of the side groups contained by the acrylamide of the copolymer, and incorporating amino groups into the particles by converting a portion of the amide groups, contained by the acrylamide of the copolymer to amino groups using the Hofmann reaction, to obtain particles having carboxyl groups and amino groups in a ratio of 0.01 to 100 carboxyl groups per one amino group;

(iii) combining the second substance with the particles having the carboxyl groups and the amino groups whereby the second substance becomes bound to the particles;

(iv) drying the particles containing the bound second substance to prepare the dry diagnostic reagent;

(b) dispersing the dry reagent in a liquid;

(c) mixing the liquid in which the diagnostic reagent is dispersed with a sample containing the first substance to bind the first substance to the second substance; and (d) optically detecting the first substance bound to the second substance contained by the diagnostic reagent.

4. The process according to claim 3, wherein the ratio of the carboxyl groups to the amino groups is 0.5 to 20 carboxyl groups per one amino group.

5. A dry detection reagent for detecting a first immunologically active substance in a sample comprising:

solid fine particles consisting of a copolymer consisting of styrene and acrylamide as copolymerized monomers containing carboxyl groups and amino groups in a ratio of from 0.01 to 100 carboxyl groups per one amino group, which are attached to a main chain of the copolymer, said solid fine particles having immobilized thereon a second substance which is immunologically active for the first substance to be detected, and said fine particles containing said immobilized second substance being in dry form.

6. A dry detection reagent for detecting a first immunologically active substance in a sample comprising:

solid fine particles consisting of a copolymer consisting of styrene and acrylamide as copolymerized monomers containing carboxyl groups and amide groups in a ratio of from 0.01 to 1,000 carboxyl groups per one amide group, which are attached to a main chain of the copolymer, said solid fine particles having immobilized thereon a second substance which is immunologically active for the first substance to be detected, and said fine particles containing said immobilized second substance being in dry form.

* * * * *

UNITED STATES PATENT AND TRADEMARK OFFICE
CERTIFICATE OF CORRECTION

Page 1 of 3

PATENT NO. : 5,656,506
DATED : August 12, 1997
INVENTOR(S) : Haruma Kawaguchi, et al.

It is certified that error appears in the above-identified patent and that said Letters Patent is hereby corrected as shown below:

On the title page, item:

[56] REFERENCES CITED

FOREIGN PATENT DOCUMENTS

"Germany ." should read --Austria .--.

COLUMN 1

Line 8, "Jul. 2," should read --Jul. 12,--;
Line 31, "quantitative" should read --a quantitative--;
Line 43, "antibody," should read --antibody--;
Line 51, "reproduced" should read --reproduced,--; and
Line 52, "impossible" should read --unsuitable--.

COLUMN 2

Line 41, "is" (second occurrence) should be deleted; and
Line 58, "for" should read --for a--.

COLUMN 3

Line 16, "one" should read --one monomer--;
Line 17, "a" should be deleted;
Line 24, "as for example" should read --as, for example,--;
Line 25, "one" should read --one monomer--; and
Line 38, "suitable" should read --suitably--.

COLUMN 4

Line 45, "groups" should read --group--;
Line 47, "carboxyl" should read --a carboxyl--;
Line 52, "it can be" should be deleted; and
Line 53, "one" should read --one monomer--.

UNITED STATES PATENT AND TRADEMARK OFFICE
CERTIFICATE OF CORRECTION

PATENT NO. : 5,656,506            Page 2 of 3
DATED        : August 12, 1997
INVENTOR(S) : Haruma Kawaguchi, et al.

It is certified that error appears in the above-identified patent and that said Letters Patent is hereby corrected as shown below:

COLUMN 5

Line 50, "α-fetogrotein," should read --α-fetoprotein,--.

COLUMN 6

Line 44, "water of" should read --water or--.

COLUMN 8

Line 51, "affecting" should read --effecting--.

COLUMN 9

Line 35, "sn" should read --an--.

COLUMN 10

Table 1, "side" should read --size--.

COLUMN 11

Line 24, "setting suitably" should read --suitably setting--.

COLUMN 12

Line 26, "more, CRP" should read --more--.

COLUMN 13

Line 23, "the" should be deleted.

UNITED STATES PATENT AND TRADEMARK OFFICE
CERTIFICATE OF CORRECTION

PATENT NO. : 5,656,506
DATED : August 12, 1997
INVENTOR(S) : Haruma Kawaguchi, et al.

It is certified that error appears in the above-identified patent and that said Letters Patent is hereby corrected as shown below:

COLUMN 14

Line 49, "of;" should read --of:--; and
    Line 52, "of;" should read --of:--.

COLUMN 15

Line 11, "of;" should read --of:--;
    Line 14, "of;" should read --of:--;
    Line 18, "carboxyl carboxyl" should read --carboxyl--;
    Line 19, "side" should read --amide--; and
    Line 22, "groups," should read --groups--.

Signed and Sealed this

Twenty-fourth Day of February, 1998

Attest:

BRUCE LEHMAN

Attesting Officer       Commissioner of Patents and Trademarks